Figure 1:
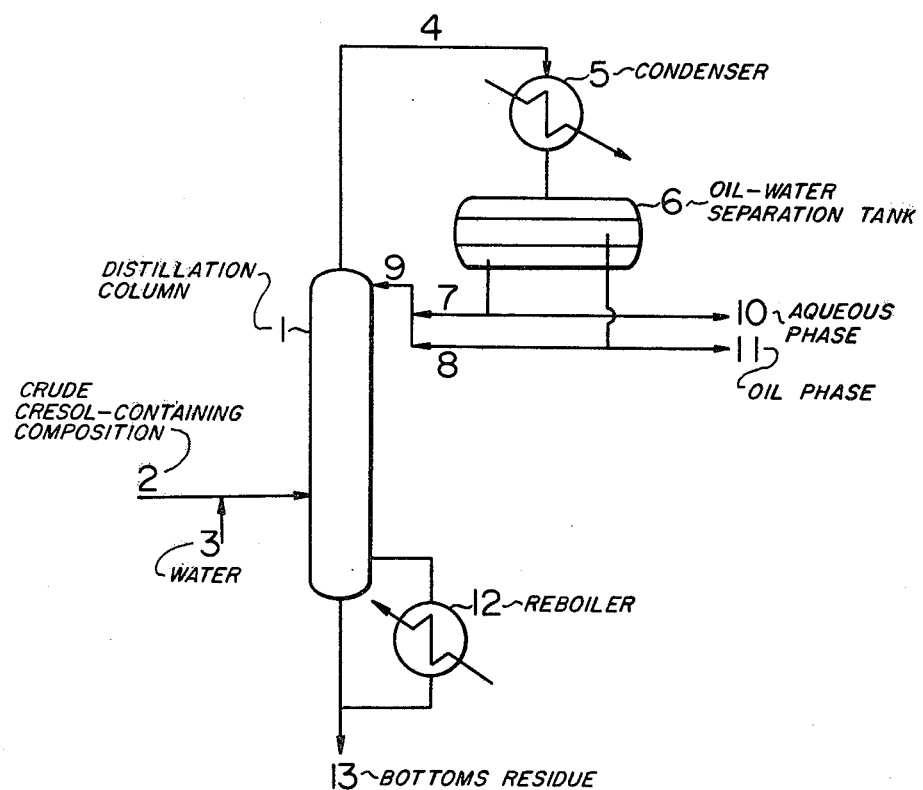

United States Patent [19]

Ohtani et al.

[11] 4,323,432
[45] Apr. 6, 1982

[54] PROCESS FOR ISOLATING AND RECOVERING META- AND PARA-CRESOLS FROM CRUDE CRESOL-CONTAINING COMPOSITIONS COMPOSED OF CRESOL COMPONENTS, UNREACTED CYMENE COMPONENTS AND HIGH-BOILING BY-PRODUCTS

[75] Inventors: Yoshitaka Ohtani, Ohtake; Junichi Nakagawa, Iwakuni, both of Japan

[73] Assignee: Mitsui Petrochemical Industries, Ltd., Tokyo, Japan

[21] Appl. No.: 165,981

[22] Filed: Jul. 7, 1980

[30] Foreign Application Priority Data

Jul. 6, 1979 [JP] Japan .................................. 54-85015

[51] Int. Cl.$^3$ .............................................. B01D 3/36
[52] U.S. Cl. ...................................... 203/85; 203/96; 568/750
[58] Field of Search ...................... 203/96, 97, 95, 92, 203/93, 98, 83, 85, 71, 79; 568/750, 749

[56] References Cited

U.S. PATENT DOCUMENTS

| | | | |
|---|---|---|---|
| 2,706,708 | 4/1955 | Frank et al. | 203/92 |
| 2,862,855 | 12/1958 | Lang et al. | 203/97 |
| 3,337,424 | 8/1967 | Neuworth et al. | 568/750 |
| 3,365,375 | 1/1968 | Nixon | 203/97 |
| 3,509,028 | 4/1970 | Budd et al. | 568/749 |

*Primary Examiner*—Wilbur L. Bascomb, Jr.
*Attorney, Agent, or Firm*—Sherman & Shalloway

[57] ABSTRACT

A improvement in the process for isolating and recovering meta- and para-cresols from crude cresol-containing compositions composed of cresol components, unreacted cymene components and high-boiling by-products, by distillation in a distillation zone, the characteristic features residing in that:

(i) the unreacted cymene components content in the crude cresol-containing composition is adjusted to 5-25% by weight of said composition after the adjustment, and the water content of said composition is adjusted to become 0.17-1.5 times by weight of the total cresol-components present in the composition, before the crude cresol-containing composition is supplied to the distillation zone, and also in that (ii) in said distillation zone, the cresol component containing ortho-cresol at a higher concentration than that in the supplied crude cresol-containing composition is distilled off as an azeotropic mixture with the unreacted cymene components and water, whereby the cresol component composed of more condensed meta- and para-cresols being isolated and recovered.

6 Claims, 1 Drawing Figure

PROCESS FOR ISOLATING AND RECOVERING META- AND PARA-CRESOLS FROM CRUDE CRESOL-CONTAINING COMPOSITIONS COMPOSED OF CRESOL COMPONENTS, UNREACTED CYMENE COMPONENTS AND HIGH-BOILING BY-PRODUCTS

This invention relates to an improvement in the process comprising subjecting a crude cresol-containing composition composed of cresol components, unreacted cymene components and high-boiling by-products having boiling points higher than that of para-cresol, to distillation under addition of water, to distil off the unreacted cymene components as an azeotropic mixture with water, whereby isolating and recovering the cresol component.

More particularly, the invention relates to an improved process for isolating and recovering meta- and para-cresols of high purity with a high recovery ratio, with an easy operation and high separating efficiency, from a crude cresol-containing composition, by distilling off ortho-cresol and unreacted cymene components as an azeotropic mixture with water.

The method of producing cresol by oxidizing cymene with a molecular oxygen-containing gas and acid cleaving the resulting cymene hydroperoxide has been recently practiced on industrial scales. The cymene to be used as the starting material is normally produced by isopropylation of toluene and which is an isomeric mixture of meta-cymene, para-cymene and a minor amount of ortho-cymene. When such an isomeric mixture of cymene is used as the starting material, the reaction product is also obtained as an isomeric mixture of meta-cresol, para-cresol and a minor amount of ortho-cresol. Ortho-cresol, however, shows a higher neural toxicity compared with other cresol isomers, and hence a cresol product substantially free of orthocresol is required for certain usages.

In the past various methods for separating ortho-cresol from cresol isomeric mixtures have been proposed, including distillation, crystallization, extraction, absorption and combination of the foregoing. With the crude cresol-containing composition to which the present invention is to be applied, i.e., the crude cresol-containing composition composed of cresol components, unreacted cymene components and high-boiling by-products having the boiling points higher than that of para-cresol, which is obtained through the process comprising oxidizing a cymene isomeric mixture with a molecular oxygen-containing gas, acid cleaving the oxidation product containing cymene hydroperoxide and removing acetone from the acid cleavage product by distillation, however, it is difficult to selectively remove ortho-cresol from its cresol components. Such attempts have been invariably accompanied with disadvantageous addition of extra operations, apparatuses or steps, or by a significant drop in the yields of object meta- and para-cresols. For example, ortho-cresol can be separated by rectification alone from a mixture composed entirely of ortho-cresol, meta-cresol and para-cresol. The crude cresol-containing composition to which the present invention is to be applied, however, is a complex mixed system containing the cresol components, unreacted cymene components, high-boiling by-products, a minor amount of water, i.e., normally up to 0.15 weight times the total cresol components and other minor components. An attempt to selectively remove orthocresol from such a composition by rectification alone, therefore, can hardly achieve the purpose because the water and cymene components form an azeotropic mixture with ortho-, meta- and para-cresols to be together distilled off. Furthermore, the object meta- and para-cresols are lost in the distilled off azeotropic mixture at a substantial ratio, considerably lowering their yields and consequently, raising their production cost.

In the art of separating a mixture of aromatic isopropyl compound and corresponding phenols into the individual components by distillation, it has been proposed to add water to the mixture before the distillation, whereby to completely distil off the aromatic isopropyl compound as an azeotropic mixture with water and recover the phenols remaining as the bottom, thus improving the separation efficiency of the two components. (see Japanese Official Patent Gazette, Publication No. 5170/55 and its U.S. Pat. No. 2,862,855, British Pat. No. 768,941).

The above literatures furthermore disclose that a mixture of 75 Kg of a cresol isomeric mixture composed of ortho-, meta, and para-cresols boiling at 192°–210° C., with 225 Kg of para-cymene and 225 Kg of water (the water content being 3 weight times the total cresol components) was distilled at 97° C. to distil off the para-cymene-water mixture, and that the cresol content in the para-cymene in said distillate was 0.04–0.08% (Example 3). In all other working examples given in the literatures, similarly three weight times the total cresol component of water was used in every run. Furthermore, the literatures are entirely silent on the technical idea of selectively distilling ortho-cresol off from the cresol isomeric mixture. As to the amount of water to be used, based on the total weight of the cresol components, again the only disclosure found in the literatures in the "three weight times" in said Example, no other descriptions being given on the optimum range of said amount. Furthermore, the literatures in nowhere refer to the mixed system containing the cresol isomeric mixture, unreacted cymene isomeric mixture, high-boiling by-products, etc., i.e., the system to which the subject invention is to be applied, but their object is to separate and recover the aromatic isopropyl compound such as cymene, in the state substantially free of phenols such as cresol which shows an inhibiting action to the liquid phase-oxidation of aromatic isopropyl compound. Hence, the literatures give no disclosure on the technical idea or means for selectively removing ortho-cresol from the cresol isomeric mixture in the specified mixed system.

We have engaged in extensive studies in search for an improved process for selectively removing ortho-cresol from a crude cresol-containing composition composed of cresol components, unreacted cymene components and high-boiling by-products having the boiling point higher than that of para-cresol, said composition having been obtained through the procedures of oxidizing a cymene isomeric mixture with a molecular oxygen-containing gas, acid cleaving the oxidation product containing cymene hydroperoxide and distilling acetone off from the acid cleavage product, by such a simple means as distillation, and separating and recovering from the system the cresol components composed mainly of meta- and para-cresols with a conspicuously reduced ortho-cresol content.

As a result we discovered that, by adjusting the amounts of the unreacted cymene components and of water in said crude cresol-containing composition to be supplied to the distillation zone to specific ranges, the loss of meta- and para-cresols at the distillation can be reduced to the minimum while selectively distilling ortho-cresol off, and hence, the bottom residue containing high purity meta- and para-cresols at high yields can be obtained. Furthermore, we discovered that meta- and para-cresols of extremely low ortho-cresol content can be easily obtained upon, for example, subjecting the bottom to distillation.

Accordingly, the object of the present invention is to provide an improved method for isolating and recovering, from the crude cresol-containing composition composed of cresol components, unreacted cymene components and high-boiling by-products, high purity meta- and para-cresols with industrial advantage, by selectively removing ortho-cresol in the aforesaid cresol components.

The above and many other objects and advantages of this invention will become more apparent from the following descriptions.

According to the present invention, an improvement of the process comprising distilling a crude cresol-containing composition composed of cresol components, unreacted cymene components and high-boiling by-products having the boiling points higher than that of para-cresol, under addition of water, said composition having been obtained through the procedures of oxidizing a cymene isomeric mixture with a molecular oxygen-containing gas, acid cleaving the oxidation product containing cymene hydroperoxide, and distilling acetone off from the acid cleavage product, to distil off the unreacted cymene components as an azeotropic mixture with water, and whereby separating and recovering the cresol component is provided, the characteristic features residing in that said distillation is practiced under the conditions meeting the following requirements (i) and (ii):

(i) before the crude cresol-containing composition is supplied to the distillation zone, its unreacted cymene components content is adjusted to 5-25% by weight of said composition after the adjustment, and the water content is adjusted to become 0.17-1.5 times by weight of the total cresol components also after the adjustment; and (ii) in said distillation zone, the cresol component containing ortho-cresol at a higher concentration than that in the supplied composition is distilled off from the system as an azeotropic mixture with the unreacted cymene components and water, whereby isolating and recovering from the system the cresol component composed of more condensed meta- and para-cresols.

The crude cresol-containing composition, to which the subject process is to be applied, is that obtained from the procedures comprising oxidizing a cymene isomeric mixture with a molecular oxygen-containing gas by the means known per se, acid cleaving the resulting oxidation product containing cymene hydroperoxide, and distilling acetone off from the acid cleavage product. As the cymene isomeric mixture, for example, that obtained by isopropylation reaction of toluene, e.g., by the reaction of toluene with propylene in the presence of a Friedel-Crafts type catalyst, is useful. Such a mixture is an isomeric mixture containing meta- and para-cymenes as the chief components, and also a minor amount of ortho-cymene.

The cymene isomeric mixture as above can be converted to the oxidation product containing the cymene hydroperoxides corresponding to said cymene isomers by the process known per se, for example, by contacting the mixture in liquid phase with a molecular oxygen-containing gas such as air, under heating at the temperatures ranging from normal temperature to approx. 200° C. The liquid phase oxidation reaction with a molecular oxygen-containing gas may also be effected by the practices known per se, for example, by stirring the system in the presence of a basic aqueous solution, i.e., an aqueous solution of an alkali metal-containing base such as lithium hydroxide, sodium hydroxide, potassium hydroxide, sodium acetate, potassium acetate, sodium propionate, potassium propionate, sodium benzoate, potassium toluate and sodium p-isopropylbenzoate; or of an alkaline earth metal-containing base such as magnesium hydroxide and barium hydroxide. Or, still other known methods using a known radical initiator or a catalyst composed of various heavy metal compounds may be employed for the liquid phase oxidation if required.

In the first mentioned embodiment, the temperature may range from, for example, approx. 60° to approx. 200° C., and in the latter case, those of normal to 200° C. can be employed. Specific examples of the radical initiator or catalyst to be used in the latter embodiment include the various compounds such as inorganic salts, organic salts and chelated complexes of various heavy metals such as copper, manganese, cobalt, nickel and iron, or hydroperoxides including cymene hydroperoxide itself.

Normally the liquid phase oxidation is effected, using a large excess of cymene. Or, the cymene may be diluted with an inert solvent such as benzene, chlorobenzene or trifluoromethylbenzene. It is recommended that the oxidation should be carried out until the cymene conversion reaches approx. 5-50%. If the oxidation is effected as a two-liquid phase system in the presence of a basic aqueous solution, first the aqueous phase is separated and removed and if necessary, the oil phase is washed with water, before it is subjected to a distillation to be freed from the solvent and the unreacted cymene, and also to be given a higher concentration level of the formed cymene hydroperoxide. The concentration level in that case is conveniently controlled so that the crude cresol-containing composition composed of cresol components, unreacted cymene components and high-boiling by-products, which is obtained upon distilling acetone off from the oxidation product containing cymene hydroperoxide and which is to be supplied to the distillation zone, would contain, based on the weight of supplied composition, 5-25%, preferably 8-20%, of the unreacted cymene components, to meet the requirement (i) of this invention. For this purpose, the distillation of the oxidation product is recommended to be continued until the solvent and unreacted cymene are distilled off and the cymene hydroperoxide content reaches approx. 3-20%, preferably approx. 6-16% by weight, of the remaining condensed oxidation product.

Thereafter the oxidation product is subjected to acid cleavage by the means known per se, for example, heating to normal temperature to approx. 100° C. in the presence of a suitable acidic catalyst such as a protonic acid, e.g., hydrochloric, sulfuric, nitric, perchloric, phosphoric or para-toluenesulfonic acid; or a solid acid, e.g., silica-alumina or silica.

The so formed acid cleavage product contains the cresol components derived from the cymene hydroperoxides corresponding to the starting cymene isomeric mixture, such as cresol isomeric mixture, and acetone.

The product furthermore contains minor amounts of by-products, such as the isomers of methylacetophenone, dimethyltolylcarbinol, isopropylbenzyl alcohol, cuminaldehyde and isopropenyl toluene. Upon neutralizing thus formed acid cleavage product with an alkali such as sodium hydroxide, potassium hydroxide, sodium carbonate or potassium carbonate, and distilling the same by the means known per se to remove acetone therefrom, the crude cresol-containing composition composed of cresol components, unreacted cymene components and high-boiling by-products having the boiling points higher than that of para-cresol is obtained.

More specifically, the composition contains, for example, meta-cresol, para-cresol, a minor amount of ortho-cresol, unreacted cymene components, traces of aromatic hydrocarbons such as isopropenyl toluene, tar-like high-boiling by-products and a minor amount of water soluble in the crude cresol-containing composition.

According to the process of this invention, water is added to the crude cresol-containing composition, which is then distilled in the distillation zone.

The distillation is effected under the conditions fulfilling the requirements (i) and (ii) of the present invention. As specified in said requirement (i), it is essential for achieving the purpose of this invention to adjust the amount of the unreacted cymene components in the composition to 5–25% by weight, based on the weight of said composition after the adjustment, as well as to adjust the amount of water to 0.17–1.5 weight times that of the total cresol components, before supplying the composition to the distillation zone.

The controlling of the unreacted cymene components content is recommendably effected at the concentration step of aforesaid oxidation product containing cymene hydroperoxide, to the operational advantage, taking into consideration in advance the expected rise in their concentration to be brought about by the acid cleavage step and acetone-removing step.

Also the controlling of water content of the composition can be effected by either adding water to the composition after the acetone-distilling off step or supplying water into the distillation zone together with the composition.

If the content of unreacted cymene components in the composition exceeds the upper limit specified in the requirement (i) of this invention, during the distilation the unreacted cymene components and other aromatic hydrocarbons such as isopropenyl toluene remain as the bottom in the distillation column, degrading the quality of object meta- and para-cresols. Whereas, when it is lower than 5% by weight, the separation efficiency of ortho-cresol in the distillation is impaired.

According to the invention, the water content in the composition to be supplied to the distillation zone should be 0.17–1.5 weight times, preferably 0.2–1 times by weight, more preferably 0.2–0.7 times by weight, the total cresol components in the composition. When the water content is less than the above-specified lower limit, the separation efficiency of ortho-cresol is impaired. Whereas, use of water exceeding the above upper limit invites no further improvement in the separation efficiency, uselessly increasing the calorific consumption for distilling off the large amount of water as an azeotropic mixture. Furthermore, because the cresol components are dissolved in the distilled water to the saturation point, the increase in the amount of distilled water results in the increased loss of the cresol components, as demonstrated in the later given Control 5 by way of example. The increase again causes the need of troublesome waste water treatment.

The "separation efficiency of ortho-cresol" mentioned herein signifies the value obtained by, separating the distillate into oil phase and aqueous phase, determining the contents of each cresol isomer in the oil phase, and calculating the mol ratio of meta- and para-cresols to ortho-cresol.

According to the invention, "the water content in the crude cresol-containing composition to be supplied to the distillation zone" signifies the total sum of the water contained in the crude cresol-containing composition obtained by distilling acetone off from the acid cleavage product, and the water added to the composition from an exterior source. The water contained in the composition as aforesaid is within the range of approx. 3 to 4.5% by weight of the composition, which corresponds to approx. 0.04–0.15 weight times of the total cresol components.

The ratio of water to the cymene components in the crude cresol-containing composition, of which unreacted cymene components content and the water content have been adjusted as specified in the requirement (i), preferably ranges from approx. 0.5–5, more preferably, from approx. 0.6–3.

According to the subject process, as specified in the requirement (ii), from the crude cresol-containing composition meeting the requirement (i), the cresol component containing ortho-cresol at a higher concentration than that in the crude cresol-containing composition is distilled off as an azeotropic mixture with the unreacted cymene components and water, and the cresol component composed of more condensed meta- and para-cresols is isolated and recovered.

The azeotropic mixture distilled off from the top of the distillation zone is separated into two phases upon cooling, one being the oil phase composed of the cresol components of increased ortho-cresol content as aforesaid and the unreacted cymene components, and the other being an aqueous phase. The distillation column for practicing the azeotropic distillation is normally operated under a suitable reflux ratio in order for improving the separation efficiency. Thus both the oil phase and aqueous phase are partly refluxed to the top of the distillation column, and the remainders, are separately withdrawn as the distillates. A part or the whole of the withdrawn aqueous phase can be recycled into the distillation column for the azeotropic distillation.

The bottoms in the distillation zone of said azeotropic distillation contain the cresol component composed substantially of meta- and para-cresol and high-boiling by-products. The bottoms can be treated by means known per se such as rectification, extraction or crystallization, allowing the isolation and recovery of a mixture composed substantially of high purity meta- and para-cresols with a high yield. Most commonly the bottoms are rectified to advantageously separate the mixture composed substantially of meta- and para-cresols.

Hereinafter the process of this invention will be explained more specifically, with reference to the working examples.

EXAMPLE 1

(1) A mixture composed of a cymene isomeric mixture containing ortho-cymene, meta-cymene and para-cymene, which had been obtained through an isopropylation of toluene, and a basic aqueous solution, was contacted with air under heating and stirring, to effect a liquid phase oxidation. The mixture after the oxidation reaction was separated into an oil phase and aqueous phase. Distilling the oil phase under a reduced pressure, the cymene hydroperoxide therein was condensed, and a mixture containing 8% by weight of cymene and 70% by weight of cymene hydroperoxide was obtained. The oxidation product was subjected to an acid cleavage in the presence of an acidic catalyst. Upon neutralizing the acid cleavage product and distilling acetone off therefrom, a crude cresol-containing composition containing 12% of cymene isomeric mixture, 1% of cresol, 35% of meta- and para-cresol mixture and 4% of water, the percentages being by weight, was obtained, the balance being composed mostly of high-boiling by-products.

(2) Into a distillation apparatus as illustrated in the attached FIG. 1, which was equipped with a distillation column 1, reboiler 12, condenser 5, oil-water separation tank 6 and refluxing devices 7, 8 and 9, the crude cresol-containing composition obtained in (1) above was supplied through a conduit 2 at a rate of 900 g per hour, and water was supplied through a conduit 3 at a rate of 30 g per hour, to effect a continuous distillation. The ratio of the total water entering into the distillation column including the water contained in the composition, to the total cresol components was 0.204 by weight. The distillate from the column top was cooled, separated into the oil phase and aqueous phase in the oil-water separation tank 6, and separately refluxed through the conduits 7, 8 and 9, respectively. The reflux ratios of the aqueous phase and oil phase were 0.4 and 1.8, respectively, and the temperature at the column top was 113° C.

The oil phase thus obtained from the conduit 11 contained cymene, a trace amount of by-product hydrocarbons and the cresol isomeric mixture, in which the mol ratio of the mixture of meta- and para-cresols to ortho-cresol was 1.40.

The ortho-cresol content of the bottoms residue obtained through the conduit 13 of the distillation column was 0.02-0.04% by weight, and no cymene was detected. By rectifying the bottoms continuously in another distillation column, a mixture of meta- and para-cresols (containing 0.03-0.06% by weight of ortho-cresol and no cymene) was obtained from the column top, and from the bottom of the column high-boiling by-products were obtained.

EXAMPLE 2

Example 1 was repeated except that the feed rate of water through the conduit 3 in the step (2) was made 190 g per hour (the weight ratio of water entering into the distillation column inclusive of the water contained in the crude cresol-containing composition, to the total cresol component was 0.70), the temperature at the column top was made 103° C., and the reflux ratios of the aqueous phase and oil phase were made 0.1 and 18, respectively.

The mol ratio of the mixture of meta- and para-cresols to ortho-cresol in the oil phase obtained from the conduit 11 (which contained cymene, by-produced aromatic hydrocarbons and the cresol isomeric mixture) was 1.35. The bottom residue contained 0.02-0.03% by weight of ortho-cresol and no cymene. By a continuous distillation of this bottom residue similar to Example 1, a mixture of meta- and para-cresols (containing 0.03-0.05% by weight of ortho-cresol and no cymene) was obtained from the column top, and from the bottom the high-boiling by-products were obtained.

EXAMPLE 3

Example 1 was repeated except that the feed rate of water through the conduit 3 in step (2) was made 290 g/hour (the weight ratio of water entering into the distillation column, inclusive of the water contained in the crude cresol-containing composition, to the total cresol component was 1.0), the temperature at the column top was made 100° C., and the reflux ratios of the aqueous phase and oil phase were made 0.1 and 1.8, respectively.

The mol ratio of the mixture of meta- and para-cresols to ortho-cresol in the oil phase obtained from the conduit 11 (which contained cymenes by-produced aromatic hydrocarbon by-products and the cresol isomeric mixture) was 1.34. The bottoms residue contained 0.02-0.03% by weight of ortho-cresol and no cymene. By a continuous distillation of the bottoms similar to Example 1, a mixture of meta- and para-cresol (containing 0.03-0.05% by weight of ortho-cresol and no cymene) was obtained from the column top, and high-boiling by-products were obtained as bottoms.

CONTROL 1

Example 1 was repeated except that no water was fed through the conduit 3 in step (2) (the weight ratio of the water entering the distillation column to the total cresol component in the composition was 0.11), the temperature at the column top was made 118° C., and the reflux ratios of the aqueous phase and oil phase were made 0.7 and 1.8, respectively.

The mol ratio of the mixture of meta- and para-cresols to ortho-cresol in the oil phase obtained from the conduit 11 (which contained cymene, aromatic hydrocarbon by-products, and the cresol isomeric mixture) was 4.2. The ortho-cresol content of the bottoms residue increased to 0.12% by weight, but the bottoms residue contained no cymene. By a continuous distillation of the bottoms similar to Example 1, a mixture of meta- and para-cresols (containing 0.18% by weight of ortho-cresol and no cymene) was obtained from the column top and high-boiling by-products were obtained as bottoms.

CONTROL 2

The step (1) of Example 1 was repeated except that the concentration level of cymene hydroperoxide, in the occasion of removing cymene from the oil phase in the oxidation reaction mixture by distillation, was controlled. Thus obtained crude cresol-containing composition contained 3% of a cymene isomeric mixture, 1.1% of ortho-cresol, 39% of a mixture of meta- and para-cresols and 4.4% of water, the percentages being by weight and the balance being mostly the high-boiling by-products.

The subsequent step (2) was practiced similar to Example 1, except that the crude cresol-containing composition as above-obtained was used, the feed rate of water through the conduit 3 was made 30 g/hour, the temperature at the column top was made 112° C. and the reflux ratios of the aqueous phase and oil phase were made 0.4 and 3.0, respectively.

The mol ratio of the mixture of meta- and para-cresols to the ortho-cresol in the oil phase obtained from the conduit 11 (which contained cymene, aromatic hydrocarbon by-products and the cresol isomeric mixture) was 2.70. The ortho-cresol content in the bottom residue was 0.08% by weight, but the bottoms contained no cymene. By a continuous distillation of the bottoms, a mixture of meta- and para-cresols (which contained 0.12% by weight of ortho-cresol and no cymene) was obtained from the column top, and high-boiling by-products were obtained as bottoms.

CONTROL 3

The step (1) of Example 1 was repeated except that the concentration level of cymene hydroperoxide, in the occasion of removing cymene from the oil phase of the oxidation reaction mixture by distillation, was controlled. Thus obtained crude cresol-containing composition contained 30% of the cymene isomeric mixture, 0.8% of ortho-cresol, 28% of a mixture of meta- and para-cresols, and 3.4% of water, the percentages being by weight and the balance being mostly the high-boiling by-products.

The subsequent step (2) was practiced as in Example 1, except that the above-obtained crude cresol-containing composition was used, the feed rate of water through the conduit 3 was made 30 g/hour, the temperature at the column top was made 114° C., and the reflux ratios of the aqueous phase and oil phase were made 0.4 and 0.8, respectively.

The mol ratio of the mixture of meta- and para-cresols to the ortho-cresol in the oil phase obtained from the conduit 11 (which contained cymene, by-produced aromatic hydrocarbons and the cresol isomeric mixture) was 1.45. The bottom residue contained only 0.02% by weight of ortho-cresol, but its contents of cymene and aromatic hydrocarbon by-products increased to 0.10% by weight. By a continuous distillation of the bottoms similar to Example 1, a mixture of meta- and para-cresols (which contained 0.03% of ortho-cresol, and 0.15% of cymene and the aromatic hydrocarbons) was obtained from the column top, and high-boiling by-products were obtained as bottoms. The product contained a large amount of neutral component, and was not a high quality product.

EXAMPLE 4

The step (1) of Example 1 was repeated except that the concentration level of cymene hydroperoxide, in the occasion of removing cymene from the oil phase in the oxidation reaction mixture by distillation, was controlled. Thus obtained crude cresol-containing composition contained 18% of a cymene isomeric mixture, 0.9% of ortho-cresol, 33% of a mixture of meta- and para-cresols, and 3.8% of water, the percentages being by weight and the balance being the high-boiling by-products.

The subsequent step (2) was repeated as in Example 1, except that the above-obtained crude cresol-containing composition was used, the feed rate of water through the conduit 3 was made 30 g/hour (the weight ratio of the water entering into the distillation column inclusive of the water contained in the composition, to the total cresol component was 0.2), the temperature at the column top was made 113° C., and the reflux ratios of the aqueous phase and oil phase were made 0.4 and 1.5, respectively.

The azeotropic mixture distilled off from the azeotropic distillation system was separated into two phases. The mol ratio of the mixture of meta- and para-cresols to the ortho-cresol in the oil phase obtained from the conduit 11 (which contained cymene, aromatic hydrocarbon by-products and the cresol isomeric mixture) was 1.42. The bottom residue contained 0.02–0.03% by weight of ortho-cresol and a trace of cymene.

By a continuous distillation of the bottoms similar to Example 1, a mixture of meta- and para-cresols (which contained 0.03–0.05% by weight of ortho-cresol and trace of cymene) was obtained from the column top, and high-boiling by-products were obtained as bottoms.

CONTROL 4

Example 1 was repeated except that in step (2), the water feed rate through the conduit 3 was made 12.6 g/hour (the weight ratio of the water entering into the distillation column inclusive of the water contained in the starting composition, to the total cresol component was 0.15), the temperature at the column top was made 116° C., and the reflux ratios of the aqueous phase and the oil phase were made 0.5 and 1.8, respectively.

The azeotropic mixture distilled off from the azeotropic distillation system was separated into two phases. The mol ratio of the mixture of meta- and para-cresols to the ortho-cresol in the oil phase obtained from the conduit 11 (which contained cymene, aromatic hydrocarbon by-products and the cresol isomeric mixture) was 2.7. The bottom residue contained 0.06–0.08% by weight of ortho-cresol and no cymene.

By a continuous distillation of this bottom similar to Example 1, a mixture of meta- and para-cresols containing 0.09–0.12% by weight of ortho-cresol and no cymene was obtained from the top of the column.

From the results of Controls 1 and 4, it can be understood that when the weight ratio of water supplied into the azeotropic distillation column inclusive of the water contained in the crude cresol-containing composition to the total cresol component in said composition becomes less than 0.17, the meta- and para-cresols contents in the azeotropic mixture distilled off from the top of the column increases, conspicuously lowering the separation efficiency of ortho-cresol.

CONTROL 5

Example 1 was repeated except that in step (2), the feed rate of water through the conduit 3 was made 612 g/hour (the weight ratio of the water entering into the distillation column inclusive of the water contained in the composition, to the total cresol component was 2), the temperature at the column top was made 100° C., and the reflux ratios of the aqueous phase and oil phase were made 0.5 and 1.8, respectively.

The azeotropic mixture distilled off from the azeotropic distillation system was separated into two phases. The mol ratio of the mixture of meta- and para-cresols to the ortho-cresol in the oil phase obtained through the conduit 11 (which contained cymene, by-produced aromatic hydrocarbons and the cresol isomeric mixture) was 1.34. The bottom residue contained 0.02% by weight of ortho-cresol, and no cymene.

By a continuous distillation of the bottoms similar to Example 1, a mixture of meta- and para-cresols containing 0.03% by weight of ortho-cresol but no cymene was obtained top of the column, and from the high-boiling by-products were obtained as bottoms.

In this Control, the weight ratio of water inclusive of the water contained in the crude cresol-containing composition to be supplied to the azeotropic distillation column, to the total cresol component in said composition was made greater than 1.5, but the mol ratio of the meta- and para-cresols mixture to the ortho phenol in the oil phase distilled off from the top of the azeotropic distillation column as an azeotropic mixture was not decreased, i.e., the separation efficiency of ortho-cresol was not improved. On the contrary, large quantities of water were distilled off as the azeotropic mixture (as large as ten times that of Example 1), containing the cresol component to the saturation point as dissolved therein. Hence, the loss of cresol component was markedly increased (approximately ten times that of Example 1). Furthermore, the large amount of distilled water containing traces of the cresol component must be treated to make it harmless as waste water. This Control also proved an additional disadvantage that a large amount of calories (approximately 4.5 times that required in Example 1, as the calories required for the entire azeotropic distillation) was consumed for distilling off the large amount of water (approx. 10 times that distilled off in Example 1).

We claim:

1. A process for isolating and recovering meta- and para-cresols comprising distilling a crude meta-, para- and ortho- cresols-containing composition obtained by acid cleaving an oxidation product containing cymene hydroperoxide formed by the oxidation of a cymene isomeric mixture with a molecular oxygen-containing gas and distilling acetone off from the acid cleavage product, said composition comprising cresol components, unreacted cymene components and high boiling by-products having boiling points higher than that of para-cresol, in the presence of water added to the distillation zone to distill off the unreacted cymene components as an azeotropic mixture with water, and isolating and recovering the cresol component, the distillation being conducted so that (i) the amount of unreacted cymene components in the crude cresol-containing composition is adjusted to 5–25% by weight of the composition after adjustment by distilling off a part of the unreacted cymenes and the water content of said cresol-containing composition is adjusted to 0.17–1.5 times by weight of the total cresol components in the composition by adding water thereto before the composition is supplied to the distillation zone; and (ii) in said distillation zone, the cresol component containing ortho-cresol at a higher concentration than that in the supplied crude cresol-containing composition is distilled off as an overhead product of the distillation zone in the form of an azeotropic mixture with the unreacted cymene components and water, whereby the cresol component composed of more concentrated meta- and para-cresols with a conspicuously reduced ortho-cresol content is isolated and recovered.

2. The process described in claim 1, in which the amount of unreacted cymene components in the crude cresol-containing composition is adjusted to 8–20% by weight of said composition after the adjustment.

3. The process described in claim 1, in which the amount of water is adjusted to 0.2–1 weight time that of the total cresol components in said composition.

4. The process described in claim 1, in which the azeotropic mixture distilled off from the top of the distillation zone is condensed into an oil phase composed of the cresol components containing ortho-cresol at a higher concentration and the unreacted cymene components, and an aqueous phase, and the distillation is effected by returning at least a part of each of the two liquid phases to the distillation zone as reflux streams.

5. The process described in claim 1, in which the azeotropic mixture distilled off from the top of the distillation zone is condensed into an oil phase composed of the cresol components containing ortho-cresol at a higher concentration and the unreacted cymene components, and an aqueous phase, and a part or the whole of the aqueous phase is recycled into the distillation zone.

6. The process described in claim 1, in which the mixture composed of meta- and para-cresols is recovered by distilling the bottoms product recovered from the distillation zone.

* * * * *